United States Patent [19]

Bush

[11] 4,263,909
[45] Apr. 28, 1981

[54] DISPENSING OF FLUENT MATERIALS

[75] Inventor: George E. Bush, Sandton, South Africa

[73] Assignee: Pitman-Moore, Inc., Washington Crossing, N.J.

[21] Appl. No.: 4,254

[22] Filed: Jan. 18, 1979

[30] Foreign Application Priority Data

Feb. 3, 1978 [ZA] South Africa .................. 78/0674

[51] Int. Cl.$^3$ ............................................. A61M 5/00
[52] U.S. Cl. ..................................... 128/215; 222/372
[58] Field of Search .... 128/218 A, DIG. 1, DIG. 18, 128/215; 222/206, 209, 214, 291, 372, 136-140; 417/477; 138/115-118

[56] References Cited

U.S. PATENT DOCUMENTS

| 2,696,173 | 12/1954 | Jensen | 417/477 |
|---|---|---|---|
| 3,386,630 | 6/1968 | Haviland | 222/309 |
| 3,679,331 | 7/1972 | Kushner | 222/214 |
| 3,737,251 | 6/1973 | Berman et al. | 417/417 |
| 3,982,534 | 9/1976 | Buckman | 222/145 |
| 4,070,725 | 1/1978 | Austin et al. | 417/477 |
| 4,155,362 | 5/1979 | Jess | 417/477 |

Primary Examiner—John D. Yasko

[57] ABSTRACT

A dispensing device for use in dispensing measured quantities of fluent materials through a plurality of resiliently compressible dispensing tubes, the device comprising a housing having a cartridge zone for receiving a cartridge having a plurality of dispensing tubes associated therewith; collapsing means for collapsing, in compression zones, dispensing tubes when located in the cartridge zone by means of a cartridge; and displacement means for displacing the collapsing means to advance the compression zones along compression paths to dispense fluent materials through such dispensing tubes.

A dispensing kit comprising a dispensing device as described, a cartridge removably located in the cartridge zone, and a plurality of resiliently compressible dispensing tubes located in the cartridge zone by means of the cartridge.

A dispensing kit comprising a dispensing device as described, a cartridge removably receivable in the cartridge zone, and a plurality of resiliently compressible dispensing tubes associated with the cartridge for positive location in the cartridge zone.

A fluent material pack for use with a dispensing device as described, and comprising a cartridge receivable in the cartridge zone of the housing of the dispensing device, and a plurality of resiliently compressible dispensing tubes associated with the cartridge.

A cartridge for use with a dispensing device as described, the cartridge comprising a body portion having a bore defined by a curved compression wall, and being adapted to have a plurality of resiliently compressible dispensing tubes associated therewith to lie along the compression wall.

17 Claims, 16 Drawing Figures

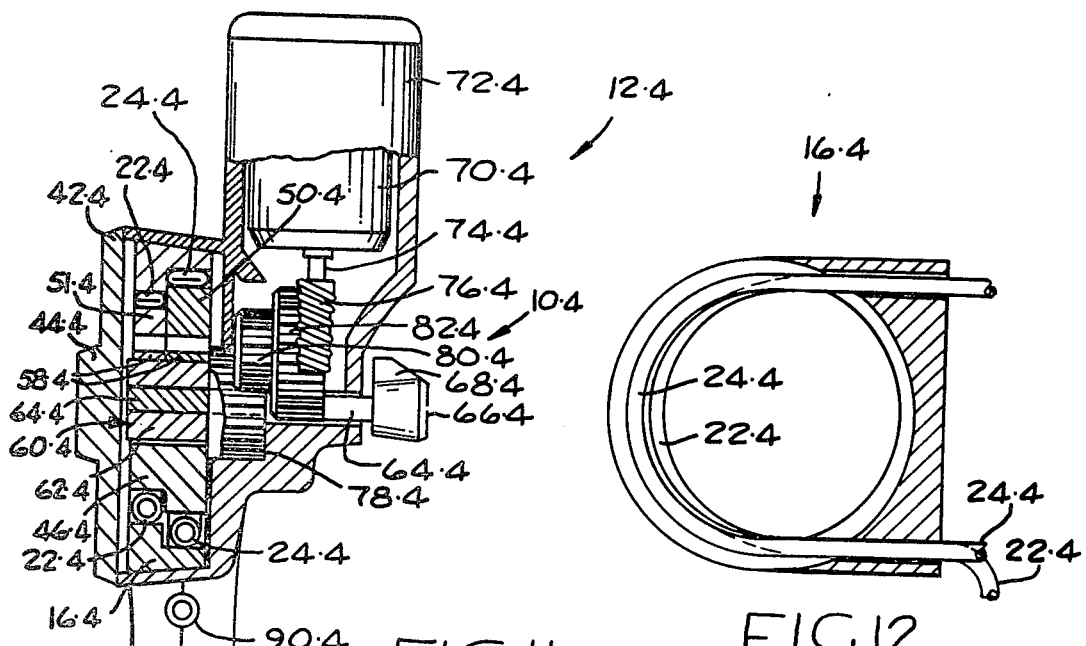
FIG. 11.
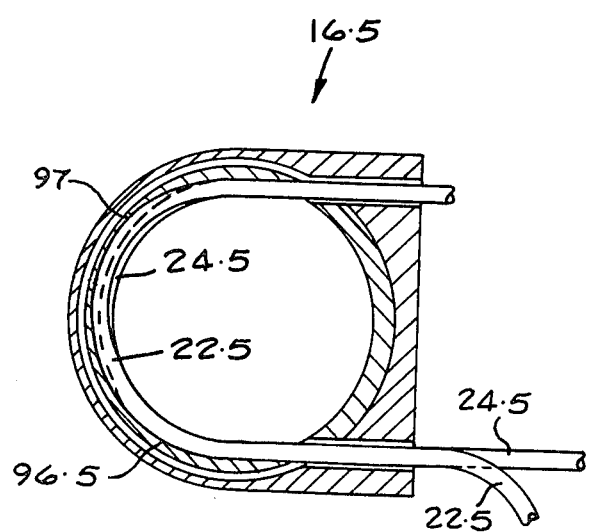
FIG. 12.
FIG. 13.

DISPENSING OF FLUENT MATERIALS

This invention relates to the dispensing of fluent materials. More particularly, this invention relates to a dispensing device for use in dispensing fluent materials, to a dispensing kit for use in dispensing fluent materials, to a fluent material pack for use with the dispensing device, and to a cartridge for use with the dispensing device.

According to the invention there is provided a dispensing device for use in dispensing measured quantities of fluent materials through a plurality of resiliently compressible dispensing tubes, the device comprising a housing having a cartridge zone for receiving a cartridge having a plurality of dispensing tubes associated therewith; collapsing means for collapsing, in compression zones, dispensing tubes when located in the cartridge zone by means of a cartridge; and displacement means for displacing the collapsing means to advance the compression zones along compression paths to dispense fluent materials through such dispensing tubes.

In an embodiment of the invention, the collapsing means may be adapted to be reciprocably displaced so that on its forward motion it will advance the compression zones along compression paths to dispense fluent material, and will then be returned to its initial position relatively to the tubes for subsequent operation.

In this embodiment of the invention, the dispensing device will include bias means to bias the collapsing means back to its inoperative or starting position.

In this embodiment of the invention, the cartridge may be adapted to locate the dispensing tubes along linear or substantially linear paths. If desired, however, the cartridge may be adapted to locate the tubes along curved paths.

In an alternative embodiment of the invention, the collapsing means may be pivotally displaceable.

Conveniently, the collapsing means may be rotatably displaceable, and the displacement means may be in the form of drive means for rotatably driving the collapsing means.

In this embodiment of the invention, the device may include control means for controlling operation of the drive means, the control means being adjustable to allow the collapsing means to be rotatably driven through a selected angle upon each actuation of the drive means.

Thus, for example, the control means may be adjustable to allow the collapsing means to be rotatably driven through a selected angle of less than 180°, through a selected angle of less than 360°, or through a selected angle of more than 360° upon each actuation of the drive means.

It will be appreciated that, if desired, the control means may be adjustable to allow the collapsing means to be rotatably driven through a selected number of revolutions upon each actuation of the drive means.

Thus by appropriately adjusting the control means, the lengths of the compression paths effected by the collapsing means upon each actuation of the drive means, can be adjusted to adjust the quantities of fluent materials dispensed by the dispensing device upon each actuation of the drive means.

In an embodiment of the invention, the drive means may comprise a displaceable lever member.

The lever member may, for example, be in the form of a manually displaceable lever member, in the form of a foot operated lever member, or the like. The lever member may be reciprocably or pivotably displaceable.

In this embodiment of the invention, the control means may be adapted to control the extent by which the displaceable lever can be displaced upon actuation thereof, thereby controlling the angle through which the collapsing means is rotatably driven upon actuation of the lever member.

In an alternative embodiment of the invention, the drive means may comprise an electric motor adapted for connection to a suitable power source.

In this embodiment of the invention, the control means may again be operatively associated with the electric motor to control pivotal displacement of the electric motor upon actuation thereof, and thus the angle through which the collapsing means is rotatably driven upon actuation of the electric motor.

The electric motor may be adapted for connection to any suitable power source such as a mains outlet, a battery, a vehicle battery, a rechargeable battery mounted on the dispensing device, or the like.

The dispensing device may include adjustment means for adjusting the effective length of at least one of the compression paths effected by the collapsing means during displacement thereof.

In an embodiment of the invention, the adjustment means may comprise an adjustable cam member to co-operate with the collapsing means and control the effective length of at least one of the compression paths during a revolution of the collapsing means.

In one example of the this embodiment of the invention, the adjustable cam member may be adapted to cooperate with the collapsing means to cause the collapsing means to be rotated eccentrically relatively to a tube located in the tube zone, with the adjustable cam member being adjustable to adjust the eccentric movement of the collapsing means and thus the effective length of a compression arc during a revolution of the collapsing means.

In an embodiment of the invention the collapsing means may include at least one radially displaceable compression member which is slidably connected to the collapsing means and projects radially beyond the periphery of the collapsing means, and the cam member may be adapted to cooperate with the compression member to control the effective length of the compression path effected by the compression member during a revolution of the collapsing means.

In a further embodiment of the invention the collapsing means may include a plurality of radially displaceable compression members which are slidably connected to the collapsing means, and the adjustment means may comprise a plurality of independently adjustable cam members to co-operate with the respective compression members.

In these embodiments of the invetion the collapsing means may include a plurality of radially displaceable compression members which are slidably connected to the collapsing means to project to differing extents beyond the periphery of the collapsing means for co-operating with dispensing tubes when located along different radii of curvature in the cartridge zone by a cartridge.

Each compression member may conveniently include bias means operative between it and the cam member to allow for manufacturing tolerances in the wall thicknesses of dispensing tubes being used in the dispensing device, to combat the compression member becoming jammed against a collapsed dispensing tube if the wall thicknesses of the tube are slightly oversize, and to combat the compression member failing to collapse a tube completely if the wall thicknesses of such a tube are slightly undersize.

The housing may conveniently have a supporting formation for supporting a dispensing nozzle on the housing.

The dispensing nozzle may be in the form of an oral dosing nozzle of any conventional type for oral administration of a veterinary remedy or the like. Alternatively, for dispensing a spot-on remedy, the dispensing nozzle may be in the form of a spot-on dispensing nozzle or lance of any conventional type.

The invention further extends to a dispensing kit comprising a dispensing device as described herein, a cartridge removably located in the cartridge zone, and a plurality of resiliently compressible dispensing tubes located in the cartridge zone by means of the cartridge.

In an embodiment of the invention the cartridge may comprise an annular ring member, the cartridge zone may have an annular recess defined in part by a cover plate for the cartridge zone, there may be two dispensing tubes having engagement flanges, and the two dispensing tubes may be located in the cartridge zone by having their engagement flanges trapped in the annular recess by the ring member located in the annular recess.

The dispensing tubes may conveniently have differing cross-sectional areas.

The invention further extends to a dispensing kit comprising a dispensing device as described herein, a cartridge removably receivable in the cartridge zone, and a plurality of resiliently compressible dispensing tubes associated with the cartridge for positive location in the cartridge zone.

The cartridge may comprise a body portion having a bore defined by a curved compression wall, and the dispensing tubes may be associated with the compression wall for compression against it by the collapsing means during use.

The dispensing tubes may conveniently have differing cross-sectional areas.

The walls of the housing defining the cartridge zone may conveniently be tapered, and the cartridge may have peripheral walls with a complementary taper to facilitate insertion and withdrawal of the cartridge relatively to the cartridge zone.

The tubes may be associated with the cartridge by any convenient means.

In one example of the invention, the dispensing tubes may be secured to the compression wall by means of a suitable adhesive.

In an alternative example of the invention, the dispensing tubes may be associated with the cartridge by the tubes having engagement flanges, and by the cartridge having complementary engagement formations engaging with the engagement flanges.

Thus, for example, the cartridge may have complementary engagement slots wherein the engagement flanges can be frictionally located, located by means of an adhesive, or located by means of at least one securing panel which can clip into the cartridge to secure the flanges of the tubes to the cartridge.

Where the tubes do have such engagement flanges, conveniently only the portions of the tubes associated with the cartridge may have the flanges, and the remaining parts of the tubes connected to either end of those portions may be formed without the flanges, or may be formed separately and secured to those portions by means of a suitable adhesive.

The dispensing tubes may, if desired, be of eliptical cross-section to facilitate collapsing of the dispensing tubes by the collapsing means during use.

By having a dispensing tube of eliptical cross-section, it will be appreciated that by varying the length of the major axis of the cross-section of the tube, the volume of fluent material dispensed by the dispensing device during use, can effectively be varied.

While the dispensing tubes of this invention are resiliently compressible to allow them to recover after compression, their walls should not be so flexible that the tubes can expand or bulge unduly during use.

At least one dispensing tube may conveniently be connected to a collapsible fluent material container. It may conveniently be integrally connected to such a container.

The fluent material container may contain a fluent material to be dispensed, so that the fluent material is housed in the container in a sterile condition when the dispensing tube is sealed by any suitable means, prior to use.

The dispensing tube and fluent material container containing the fluent material, can thus be supplied in a sterile sealed condition.

In an embodiment of the invention the cartridge may have a dispensing nozzle integrally mounted thereon, and the dispensing tubes may lead to the nozzle.

In an embodiment of the invention, where the fluent material is to be in the form of an injectable solution or an injectable slurry, the dispensing tubes may form a common discharge tube beyond the cartridge, and a needle or a floating needle may be operatively mounted at the free end of discharge tube.

In an embodiment of the invention, the floating needle may be integrally mounted on the tube, for disposal with the tube and fluent material container after use.

The needle, or the dispensing nozzle, as the case may be, may conveniently incorporate a one-way valve having a closure member which is biassed to combat dripping under the action of gravity when the device is not in use.

In an embodiment of the invention, the control means of the dispensing device may comprise a control circuit and a plurality of displaceable micro switches which are adapted to be actuated to actuate the control circuit, the control means being such that each displaceable switch will, upon actuation, cause the control means to allow the collapsing means to be rotatably driven through an angle which is specific for that displaceable switch.

In one example of this embodiment of the invention, the displaceable micro switches may be positioned at circumferentially spaced intervals for selective actuation by a pivotally displaceable control knob which is mounted on the device and has an actuating pointer mounted thereon.

In an alternative example of this embodiment, the micro switches may be mounted at spaced intervals in the housing adjacent the cartridge zone, and the cartridge may be provided with actuating pointers which are positioned to co-operate with the switches upon location of the cartridge in the cartridge zone.

In this example of the invention, depending upon the required angle through which the collapsing means is to be driven upon each actuation of the drive means for the particular fluent materials to be dispensed, the cartridge may be provided with a single appropriately positioned actuating pointer, or the inappropriate actuating pointers may be broken off prior to use.

In an embodiment of the invention, the cartridge may include a one-way valve having a valve closure member which is biassed to combat discharge of fluent materials through the dispensing tubes under gravity.

In this embodiment of the invention the kit may, for example, include a main dispensing tube and a secondary dispensing tube, and the valve may have a main inlet sleeve to which the main dispensing tube is connected, and a secondary inlet sleeve to which the secondary dispensing tube is connected.

In an embodiment of the invention the dispensing tubes may be associated with the cartridge such that their effective lengths presented for compression during use, will differ.

The invention further extends to a fluent material pack for use with a dispensing device as described herein, and comprising a cartridge as described herein receivable in the cartridge zone of the housing of the dispensing device, and a plurality of resiliently compressible dispensing tubes associated with the cartridge.

The dispensing tubes may be associated with the cartridge by any suitable means as hereinbefore described, and the dispensing tubes may be associated with a fluent material pack or the like, as hereinbefore described.

The invention further extends to a cartridge for use with a dispensing device as described herein, the cartridge comprising a body portion having a bore defined by a curved compression wall, and being adapted to have a plurality of resiliently compressible dispensing tubes associated therewith to lie along the compression wall.

The cartridge may have a dispensing nozzle integrally mounted thereon, the dispensing nozzle having coupling means for coupling dispensing tubes associated with the cartridge, thereto.

Usually, the dispensing device of this invention will be used for dispensing two different liquids or slurries in a required proportion to each other. It will be appreciated however, that this invention can equally be applied to the dispensing of fluent materials from three or more tubes in desired proportions.

The dispensing device of this invention may be in the form of a gun with a handle portion to allow it to be handled for use.

In an alternative embodiment of the invention, the dispensing device of this invention may be in the form of a unit to be placed at a suitable location or to be suspended on the body of an operator.

In this embodiment of the invention, the device may include an actuating member which may be actuated at a point remote from the device to actuate the device.

The actuating member may include a needle or a dispensing nozzle, may be of a suitable shape to be held by hand, and may have the free ends of the dispensing tubes or the free end of a common discharge tube located therein.

This invention can have application wherever two or more fluent materials are to be dispensed in desired relative proportions, particularly where the fluent materials are required to be dispensed in particular successive dosages.

Thus, for example, the invention can have application in dispensing different chemical substances, in dispensing different chemical substances, in dispensing veterinary remedies, pesticides, toxic substances, dosing materials, medicines, and the like.

In conventional applications for veterinary remedies and the like, the usual concentrations which would be desirable, would require dilution of between about 4:1 and 10:1 by volume with water.

Dilutions of this order can readily be effected by appropriate selection of effective compression lengths and/or tube cross-sectional areas.

In an embodiment of the invention, a back pack may be used in the dispensing kit, which has separate compartments, the one for containing the active ingredient, and the other for containing the diluent or the substance to be mixed with the active ingredient.

In an embodiment of the invention, where the device is to be used for oral dosing of a veterinary remedy, the dispensing device may be set so that the active ingredient will be mixed with the required proportion of water during portion of the cycle of the collapsing means, whereafter no further active ingredient will be dispensed during the remainder of the cycle, but water alone will be dispensed to serve as a purging dose and combat loss of active ingredient as a result of spitting.

Embodiments of the invention are now described by way of example with reference to the accompanying drawings.

In the drawings

FIG. 11 shows a view corresponding to that of FIG. 10, of yet a further alternative embodient of a dispensing kit in accordance with this invention;

FIG. 12 shows a diagrammatic, fragmentary, underside plan view of the cartridge of the dispensing kit of FIG. 11;

FIG. 13 shows a diagrammatic, fragmentary, sectional plan view of an alternative embodiment of a cartridge to form part of the fluent material pack of this invention;

Figure 1:
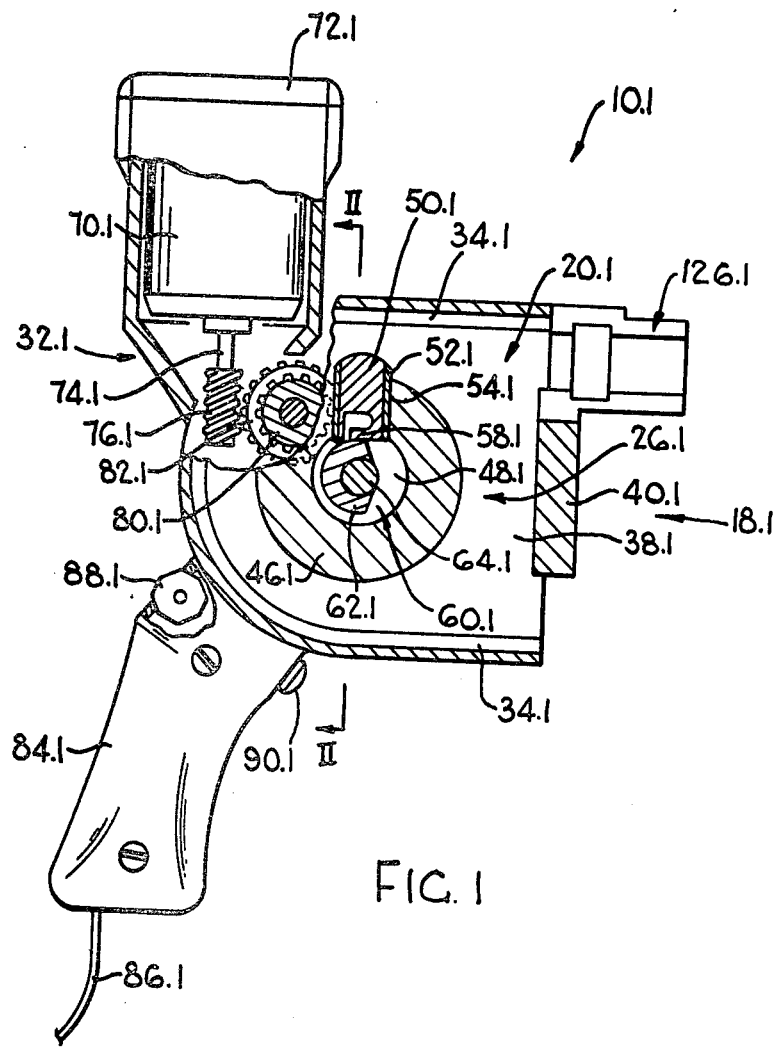
FIG. 1 shows a diagrammatic, fragmentary partly sectional side elevation along line I—I of FIG. 2, of one embodiment of a dispensing device in accordance with this invention for use in dispensing measured quantities of fluent materials through two resiliently compressible dispensing tubes.
Figure 2:
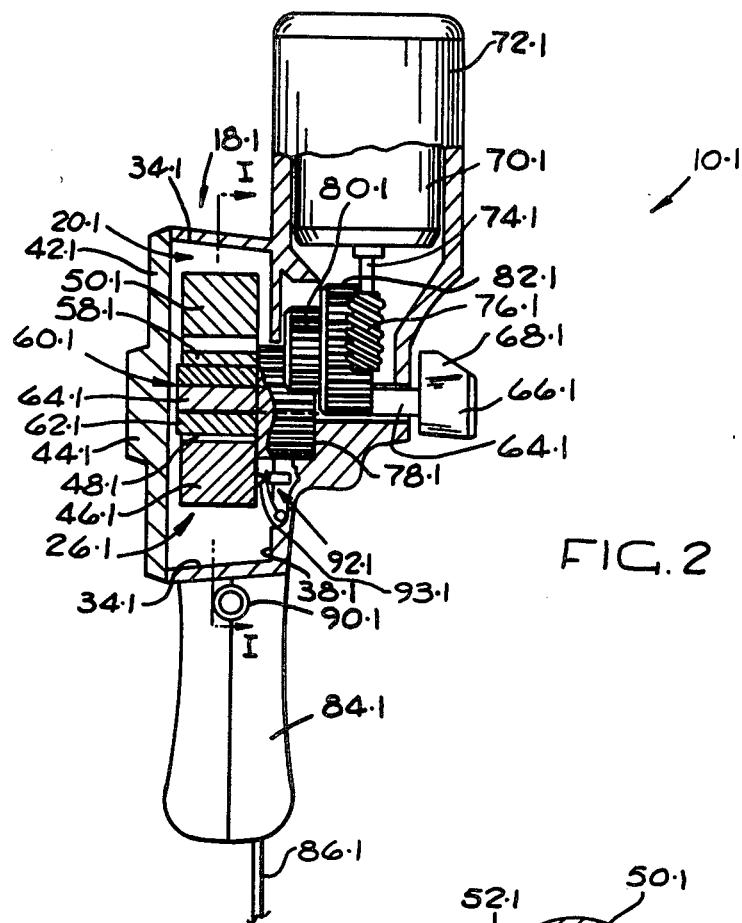
FIG. 2 shows a diagrammatic, fragmentary, partly sectional front elevation along line II—II of FIG. 1, of the dispensing device of FIG. 1.
Figure 3:
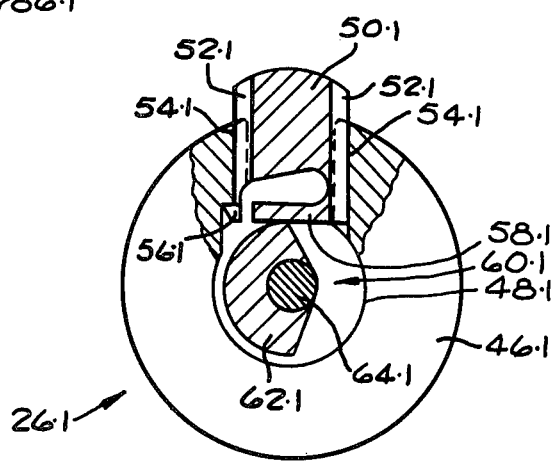
FIG. 3 shows, to an enlarged scale, a fragmentary partly sectional side elevation of the collapsing means and the adjustment means of the dispensing device of FIG. 1.

With reference to FIGS. 1 to 3 of the drawings, reference numeral 10.1 refers generally to a dispensing device for use in dispensing measured quantities of fluent materials through two resiliently compressible dispensing tubes.

Figure 6:
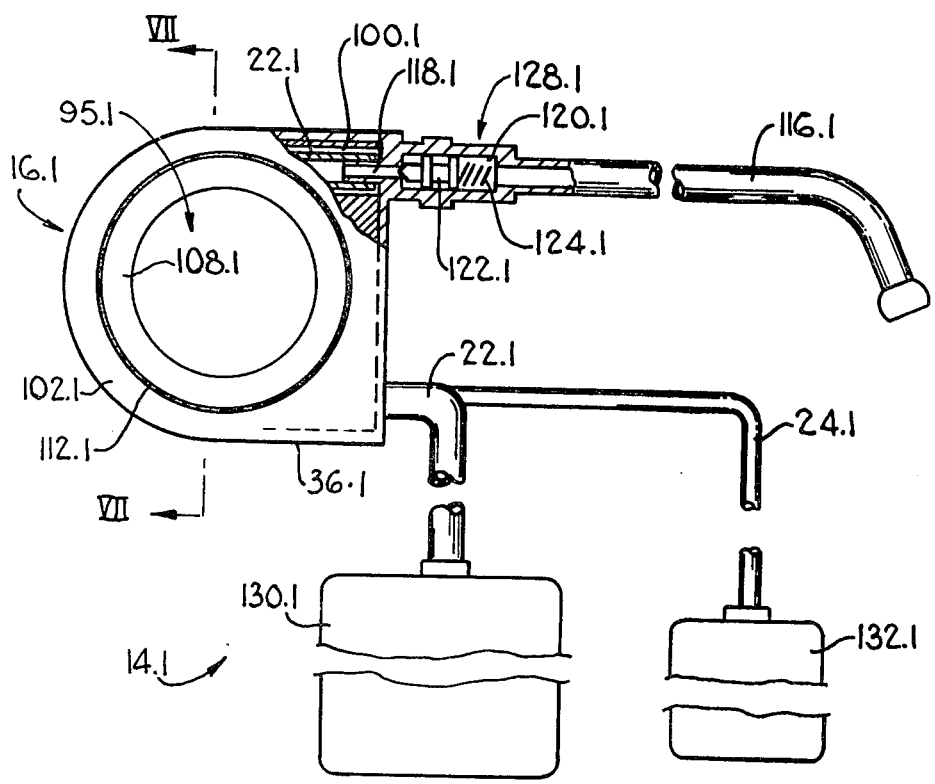
FIG. 6 shows a fragmentary, partly sectional, diagrammatic view of an alternative embodiment of a fluent material pack for use with the dispensing device of this invention.

With reference to FIGS. 8 and 9, and FIGS. 6 and 7 of the drawings, reference numeral 12.1 refers generally to a dispensing kit in accordance with this invention, comprising the dispensing device 10.1 of FIGS. 1 and 2, removably loaded with a fluent material pack 14.1 as illustrated in FIG. 6 of the drawings.

Figure 7:
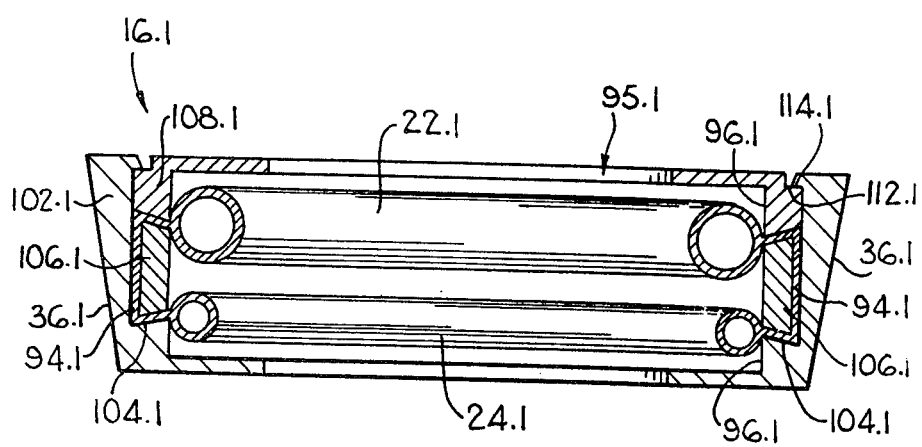
FIG. 7 shows, to an enlarged scale, a sectional view of portion of the fluent material pack of FIG. 6, along line VII—VII of FIG. 6.

The fluent material pack 14.1 includes a cartridge 16.1 as illustrated in FIGS. 6 and 7 of the drawings.

With reference to FIGS. 1 to 9 of the drawings, the dispensing kit 12.1 is suitable for use in dispensing a veterinary remedy which is provided in concentrated form, simultaneously with a diluent in the form of water, in predetermined portions so that the diluted veterinary remedy which is dispensed, will be at the correct concentration for a required dosage rate.

It will be appreciated, however, that the dispensing kit 12.1 may be used in the same way for dispensing two different veterinary remedies simultaneously.

The dispensing device 10.1 comprises a housing 18.1 having a cartridge zone 20.1 for removably receiving the cartridge 16.1 which has two resiliently compressible dispensing tubes 22.1 and 24.1 mounted thereon.

The dispensing device 10.1 further comprises collapsing means 26.1 for collapsing, in compression zones 28.1 and 30.1, the dispensing tubes 22.1 and 24.1 when located in the cartridge zone 20.1 by means of the cartridge 16.1; and displacement means in the form of drive means 32.1 for rotatably displacing the collapsing means 26.1 to advance the compression zone 28.1 and 30.1 along compression paths to dispense fluent materials through the dispensing tubes 22.1 and 24.1.

The cartridge zone 20.1 is defined by a tapered peripheral wall 34.1 which has a complementary taper to that of an outer peripheral wall 36.1 of the cartridge 16.1 (FIG. 7) thereby facilitating loading of the cartridge 16.1 into the cartridge zone 20.1, and removal of the cartridge therefrom.

The cartridge zone 20.1 is further defined by a base wall 38.1 and a front wall 40.1.

Figure 9:
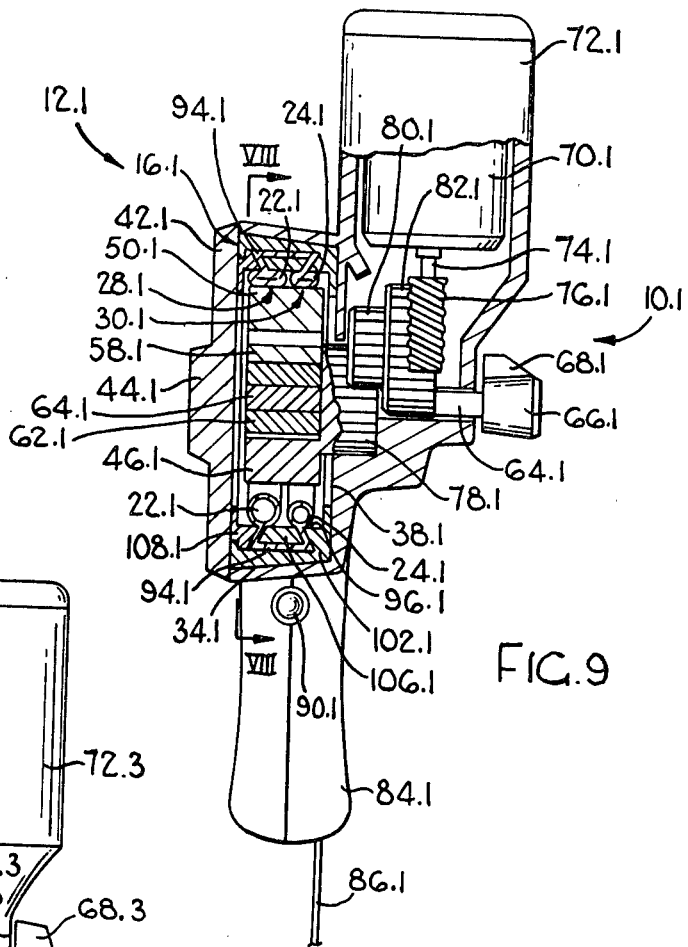
FIG. 9 shows a diagrammatic, partly sectional, front elevation of the dispensing kit of FIG. 8, along line VIX—VIX of FIG. 8.

As can be seen in FIGS. 2 and 9, the dispensing device 10.1 further includes a removable cover plate 42.1 having a knob 44.1 which can be held for applying or removing the cover plate 42.1.

Once the cartridge 16.1 has been located in position in the cartridge zone 20.1, the cover plate 42.1 can be fixed to the housing 18.1 to close the cartridge zones 20.1 and firmly locate the cartridge 16.1 therein.

The dispensing device 10.1 includes a securing screw (not shown) for securing the cover plate 42.1 in its operative position.

The collapsing means 26.1 comprises a single rotary member 46.1 having a hollow bore 48.1.

The rotary member 46.1 has one radially displaceable compression member 50.1 slidably mounted thereon for displacement in the radial direction relatively to the axis of the rotary member 46.1

As can be seen in particular in FIG. 3, the compression member 50.1 has opposed flanges 52.1 which are slidably located in complementary slots 54.1 in the rotary member 46.1 to allow the compression member 50.1 to be slidably displaced in the radial direction.

The compression member 50.1 has a hook 56.1 which co-operates with the rotary member 46.1 to locate the compression 50.1 against complete withdrawal from the rotary member 46.1.

The compression member 50.1 is formed with a resilient portion 58.1 which is resiliently flexible to serve the purpose as will be hereinafter described.

The compression member 50.1 is formed out of a self-lubricating synthetic plastics material to reduce frictional resistance between it and the dispensing tubes 22.1 and 24.1 during use. If desired, however, a suitable lubricant may be applied to the portions of the dispensing tubes 22.1 and 24.1 which will co-operate with the compression member 50.1, prior to use of the cartridges 16.1.

The dispensing device 10.1 further includes adjustment means for adjusting the effective lengths of the compression paths effected by the compression member 50.1 during rotational displacement of the rotary member 46.1.

The adjustment means comprises a single adjustable cam member 60.1 which has a camming surface 62.1 extending through an angle of 180°.

The cam member 60.1 with its camming surface 62.1 is located within the hollow bore 48.1 and is mounted on an adjustment shaft 64.1 which extends therefrom through a suitable bore in the housing 18.1.

The adjustment shaft 64.1 terminates in an adjustment knob 66.1 having a pointer 68.1.

Figure 8:
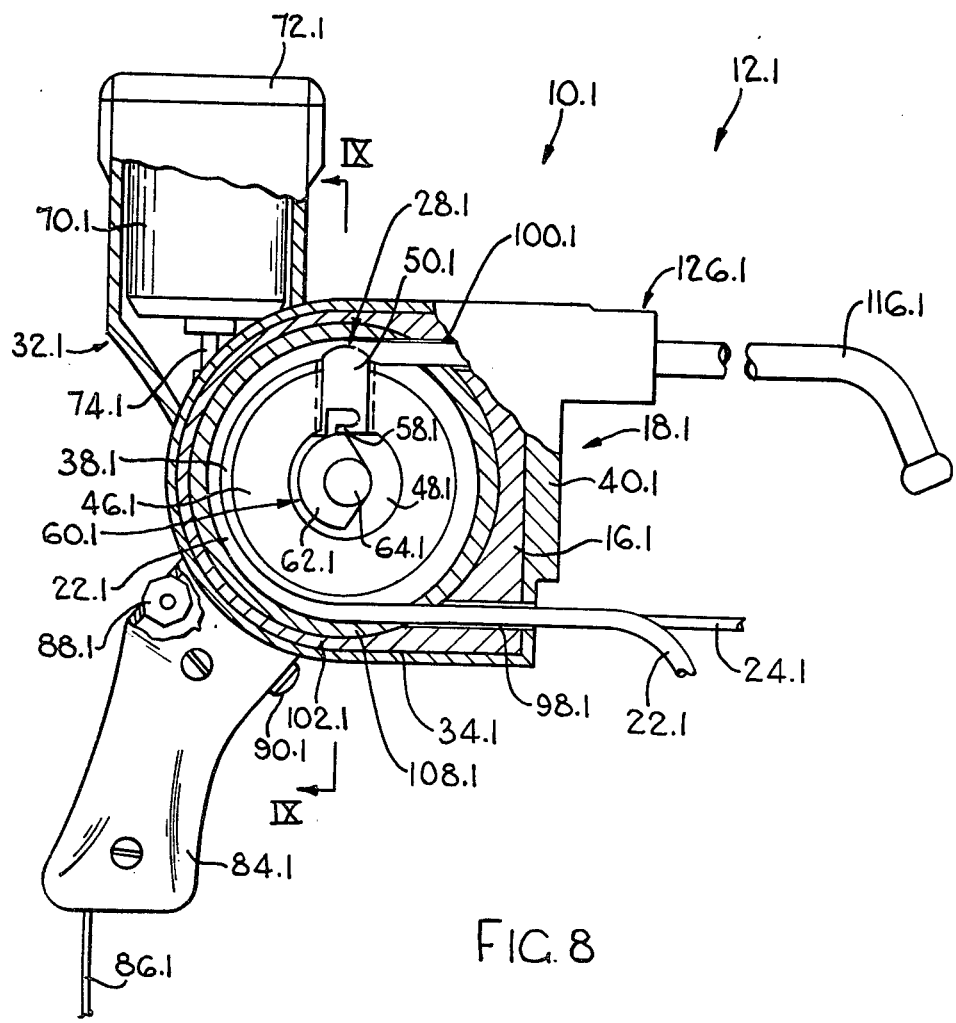
FIG. 8 shows a diagrammatic, fragmentary, partly sectional side elevation along line VIII—VIII of FIG. 9, of one embodiment of a dispensing kit in accordance with this invention, comprising of the dispensing device of FIGS. 1 and 2 having the fluent material pack of FIG. 6 removably associated therewith.

In use, if the rotary member 46.1 is rotatably driven by the drive means 32.1, with the cam member 60.1 in its position as shown in FIGS. 1, 2, 8, and 9, the compression member 50.1 will co-operate with the camming surface 62.1 so that the camming surface will force the compression member against the tubes 22.1 and 24.1 to collapse the tubes in compression zones 28.1 and 30.1 vertically below the central axis of the cam member 60.1 when the rotary member 46.1 is rotated in a clockwise direction, as viewed in FIGS. 1 and 8. Thereafter, the compression zones will be advanced by the compression member 50.1 through an arc of 180° until the compression member 50.1 reaches the position vertically above the axis of the cam member 60.1, as shown in FIGS. 1, 2, 8, and 9.

However, if the adjustable cam member 60.1 is pivotally displaced through an angle of 90° from the position illustrated in the drawings, and is located in such new position, the cam will only be effective in forcing the compression member 50.1 against the tubes 22.1 and 24.1 to collapse the tubes, through an arc of 90°.

It follows that the quantities of fluent materials dispensed through the tubes 22.1 and 24.1 during such a revolution of the rotary member 46.1 will be half the quantities previously dispensed when the compression arc extended through an angle of 180°.

In this way, by adjusting the position of the adjustable cam member 60.1, the quantities of fluent materials dispensed through the tubes 22.1 and 24.1 on each revolution of the rotary member 46.1, can be varied as required.

Markings relating to different masses of animals to be treated with a particular veterinary remedy, may be marked on the outside of the dispensing device 10.1. Thus, with the aid of the pointer 68.1, the adjustment knob 66.1 can be adjusted for an appropriate quantity of fluent material to be dispensed per revolution in relation to the estimated mass of an animal to be treated.

The camming surface 62.1 co-operates with the resilient portion 58.1 to displace the compression member 50.1 radially outwardly during use.

The resilient portion 58.1 therefore allows for manufacturing tolerances in the wall thicknesses of the dispensing tubes 22.1 and 24.1 to combat the compression member 50.1 becoming jammed against the collapsed tubes if the wall thicknesses are slightly oversize, and to combat failure to collapse the tubes sufficiently if the wall thicknesses of the tubes are slightly undersize.

The drive means 32.1 as illustrated in the drawings, comprises an electric motor 70.1 mounted in a motor housing 72.1 which extends upwardly from the housing 18.1. The motor 70.1 has a drive shaft 74.1 extending therefrom, and a gear 76.1 is mounted on the drive shaft.

The rotary member 46.1 has an annular gear 78.1 provided thereon below the hollow bore 48.1. The annular gear 78.1 has a bore through which the adjustment shaft slidably extends.

The annular gear 78.1 and the gear 76.1 are operatively coupled by means of a gear train 80.1 and 82.1.

The dispensing device 10.1 includes a handle 84.1 which is integral with the housing 18.1. The handle 84.1 is shaped and the size and mass of the dispensing device 10.1 are such that it can readily be held in one hand for use.

An electrical lead 86.1 extends out of the handle 84.1 for connecting the motor 70.1 to a suitable source of electrical power.

The dispensing device 10.1 includes control means which is mounted in the handle 84.1 for controlling operation of the motor 70.1 to allow the motor to rotatably drive the rotary member 46.1 through a selected number of revolutions upon each actuation of the motor 70.1.

The control means comprises a control circuit of any suitable conventional type, which includes a plurality of displaceable micro switches (not shown) which are adapted to be selectively actuated to actuate the control circuit, the control means being such that each displaceable switch will, on actuation, cause the control means to allow the motor 70.1 to rotatably drive the rotary member 46.1 through a number of revolutions specific for that displaceable switch.

The displaceable micro switches are mounted at circumferentially spaced intervals for selective actuation by a pivotally displaceable control knob 88.1 (FIGS. 1 and 8) which is mounted in the handle 84.1 and which has an actuating pointer for actuating the micro switches.

In the embodiment illustrated in the drawings, the control circuit includes seven micro switches, and the control knob 88.1 has eight stations. The control knob 88.1 can thus be positioned in a first station where none of the micro switches are actuated, in a second station where the micro switch which will cause a single revolution of the rotary member 46.1 is actuated, and so on until the eighth station where, upon actuation of the control circuit, the rotary member 46.1 will be driven through seven revolutions.

The control circuit includes an actuating trigger 90.1 which is mounted on the handle 84.1 for actuating the control circuit.

The control circuit further includes a counter of conventional type to count the number of revolutions of the rotary member 46.1 upon actuation of the control circuit, to allow the control circuit to cease operation once the dictated number of revolutions have occurred.

The counter is actuated by means of a micro switch 92.1 (as shown only in FIG. 2) in the base wall 38.1.

The rotary member 46.1 has a pointer 93.1 (as shown in FIG. 2 only) mounted on its lower surface to actuate the micro switch 92.1 once during each revolution.

Thus, by suitably setting the control knob 88.1, the dispensing device 10.1 can be operated by actuation of the trigger 90.1, so that a desired number of revolutions are performed by the rotary member 46.1 for each actuation of the trigger. Thus, desired quantities of fluent material can be dispensed upon each actuation of the trigger 90.1.

Those portions of the dispensing tubes 22.1 and 24.1 which are associated with the cartridge 16.1, are integrally connected to each other by means of an engagement flange 94.1 for use in securing the dispensing tubes to the cartridge 16.1.

The cartridge 16.1 comprises a body portion having a bore 95.1 defined a semi-circular compression wall 96.1 against which the dispensing tubes are compressed by the compression member 50.1 during use to dispense fluent materials through the dispensing tubes during rotation of the rotary member 46.1.

The cartridge 16.1 has inlet and outlet threading apertures 98.1 and 100.1 leading to the compression wall 96.1, and through which the dispensing tubes are threaded.

The cartridge 16.1 has an outer wall 102.1 which has an angled shoulder 104.1.

The cartridge further comprises a removable annular clamping ring 106.1 which has its opposed ends tapered for the purpose as will be hereinafter described.

The cartridge further includes a removable annular locking ring 108.1. The annular locking ring has a tapered lower surface 110.1, and has an annular shoulder 112.1 to co-operate with a complementary shoulder 114.1 provided on the outer wall portion 102.1.

Thus, to locate the tubes 22.1 and 24.1 in position on the cartridge 16.1, the engagement flange 94.1 can be located on the inner surface of the outer wall 102.1, whereafter the annular clamping ring 106.1 can be fitted, and then the annular locking ring 108.1 can be fitted in position with the annular shoulder 112.1 co-operating with the complementary annular shoulder 114.1. Thus, in this position, the engagement flange 94.1 is firmly clamped to the cartridge 16.1.

In view of the angled shoulder 104.1, the tapered surfaces of the clamping ring 106.1, and the tapered lower surface 110.1 of the locking ring 108.1, the dispensing tubes 22.1 and 24.1 will be firmly located in the cartridge 16.1 against displacement and, in particular, against axial displacement during use.

The mounting of the dispensing tubes 22.1 and 24.1 on the cartridge 16.1 not only provides the advantage that the dispensing tubes will be firmly located against displacement during use, but also that loading and unloading of the tubes into the dispensing device 10.1 is facilitated because of the cartridge 16.1 which can be readily loaded and unloaded, and which can fit into the cartridge zone 20.1 only in the correct position and attitude.

The cartridge 16.1 has a dispensing nozzle 116.1 integrally formed therewith to extend therefrom.

The dispensing nozzle 116.1 is in the form of a nozzle for oral dosing.

The dispensing nozzle 116.1 has inlet sleeves 118.1 (only one being visible) as shown in FIG. 6, to which the discharge ends of the tubes 22.1 and 24.1 are connected.

The inlet sleeves 118.1 lead to a mixing chamber 120.1 before discharge from the nozzle 116.1.

In the embodiment illustrated in FIG. 6 of the drawings, the mixing chamber 120.1 includes a valve closure member 122.1 (FIG. 6) which is biassed by means of a spring 124.1 to co-operate with the inlet sleeves 118.1 thereby combatting discharge of fluent materials through the dispensing tubes under gravity when the cartridge 16.1 is not in use.

In an alternative embodiment of the invention, if desired, a corresponding one-way valve may be position at the discharge end of the dispensing nozzle 116.1 instead of in the mixing chamber 120.1.

It will be appreciated that the dispensing nozzle 116.1, instead of being in the form of an oral dosing nozzle, may be in the form of a lance for applying a spot-on veterinary remedy. Such a lance may again have a one-way valve mounted at its leading end.

The housing 18.1 of the dispensing device 10.1 has a supporting formation 126.1 which is in the form of a semi-circular trough.

The cover plate 42.1 has a complementary supporting formation (not shown) to co-operate with and complete the supporting formation 126.1.

The casing 128.1 defining the mixing chamber 120.1 has a complementary shape. Thus, when the cartridge 16.1 is located in the cartridge zone 20.1, the casing 128.1 will be located in the supporting formation 126.1. When the cover plate has been fixed in position, the casing 128.1 and thus the nozzle 116.1 will be firmly located in the complete supporting formation 126.1, thereby combatting any tendency for the dispensing nozzle 116.1 to break off from the cartridge 16.1 during use.

The dispensing tubes 22.1 and 24.1 are formed out of a resiliently compressible synthetic plastics material and are of a convenient length for effective use. The synthetic plastics material is such that the tubes can be resiliently compressed during use, and will recover after compression, but the material is not so flexible that the tubes will expand or bulge unduly under pressure.

With particular reference to FIG. 6 of the drawings, the fluent material pack 14.1 comprises the cartridge 16.1, the dispensing nozzle 116.1, the dispensing tubes 22.1 and 24.1, and two collapsible fluent material containers 130.1 and 132.1.

The dispensing tube 22.1 is sealingly connected to the container 130.1, whereas the tube 24.1 is sealingly connected to the container 132.1.

The container 130.1 contains water, whereas the container 132.1 contains the required veterinary remedy.

Instead of the container 130.1 being in the form of a collapsible container, it may be in the form of a rigid container which may be suspended on the body of an operator.

Where the container is rigid, it may have a filling opening with a closure cap which allows air to bleed into the container during use, thereby combatting the establishment of a reduced pressure within the container.

In use, a selected veterinary remedy can be provided in the container 132.1 in a sterile condition. Thereafter the dispensing tube 24.1 can be fixed to the container 132.1.

Since the tube 24.1 is sealed by means of a one-way valve, the veterinary remedy will be stored in the container 132.1 in a sterile condition.

When the system is required for use, the cartridge 16.1 can be readily and quickly located in the dispensing device 10.1, and the tube 22.1 can be sealingly connected to the container 130.1 which is filled with water which is sufficiently sterile.

The fluent material pack 14.1 will therefore remain sterile until it is required for use. Since the veterinary remedy is provided in a concentrated form in the collapsible container 132.1, this will reduce the cost of transport and will further facilitate sterilisation of the remedy to combat deterioration during storage or transportation, and prior to use.

By selecting the tubes 22.1 and 24.1 with an appropriate cross-sectional bore area relationship between them, when the fluent material pack 14.1 is used, the concentrated veterinary remedy and the water from the containers 132.1 and 130.1 respectively, will be dispensed in a definite and predetermined proportion.

Thus, the concentrated veterinary remedy will be diluted in the appropriate proportion, and dilution will occur on the downstream side of the cartridge 16.1 immediately prior to use of the diluted veterinary remedy.

Even if the water is therefore contaminated to the extent that it can cause deterioration of the veterinary remedy, this will not be material since the diluted remedy is used immediately it is mixed with water, and is otherwise maintained completely separate from the water.

It is therefore an advantage of the embodiment of the invention as illustrated in FIGS. 1 to 9 of the drawings that a veterinary remedy can be stored in a concentrated and sterile condition and yet is readily available for use.

The embodiment as illustrated provides the further advantage that the veterinary remedy can be supplied as part of the fluent material pack thereby permitting use without any undue risk of skin contact with the veterinary remedy.

The embodiment as illustrated in the drawings can provide the further advantage that by appropriate selection of the cross-sectional areas of the dispensing tubes 22.1 and 24.1, it can be ensured that dilution of the concentrated veterinary remedy will be effected automatically and in the correct proportions, and that contamination of the veterinary remedy and the dangers of physical contact on dilution or mixing, can be reduced if not totally eliminated.

The embodiment of the invention as illustrated in the drawings provides the further advantage that the cartridge 16.1 can be easily and effectively loaded into the dispensing device, and unloaded from the dispensing device.

The embodiment of the invention as illustrated in the drawings provides the further advantage that by means of the control circuit and the control knob 88.1, the quantity of diluted veterinary remedy dispensed for each actuation of the control circuit by means of the trigger 90.1, can be readily and effectively adjusted over a reasonable range.

The embodiment as illustrated in the drawings provides the further advantage that by adjusting the cam member 60.1, the quantity of diluted veterinary remedy dispensed for each revolution of the rotary member 46.1, can be readily and effectively adjusted.

In practice therefore, it will be necessary to ensure that the concentration of the veterinary remedy is appropriate in relation to the relationship between the bore cross-sectional areas of the dispensing tubes 24.1 and 22.1 so that the concentrated veterinary remedy will be diluted in the appropriate proportion during use. Thereafter, by appropriate adjustment of the cam member 60.1 and the control knob 88.1, the dosage rate can be varied over a wide range to cater for the usual range of dosage rates which will be required during use.

The embodiment of the invention as illustrated in these Figures of the drawings, provides the further advantage that since the compression member 50.1 co-operates slidably with the dispensing tubes under the biassing action of the resilient portion 58.1, it should not tend to be subject to undue wear. If the tubes 22.1 and 24.1 do become worn, this is of no consequence since they should last for a sufficient period to allow the active ingredient contained in the container 132.1 to be dispensed, and can then be discarded.

This can therefore provide the further advantage that even abrasive slurries and the like can be dispensed by means of the dispensing kit 12.1.

In an alternative embodiment of the invention, if it is found that the compression member 50.1 does become subject to wear, it can instead by replaced by a more robust biassing arrangement than the resilient portion 58.1 and, in addition, a roller may be mounted at the operative end of the compression member 50.1 to co-operate with the dispensing tubes.

Figure 4:
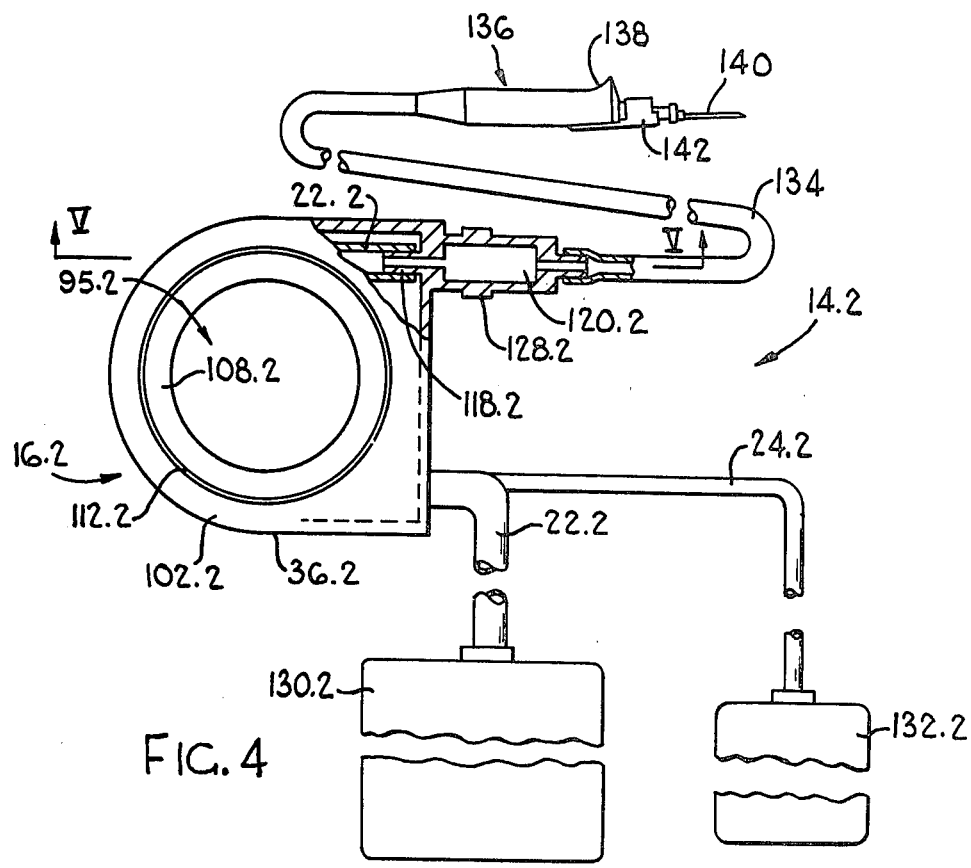
FIG. 4 shows a diagrammatic, fragmentary, partly sectional side elevation of one embodiment of a fluent material pack for use with the dispensing device of this invention.
Figure 5:
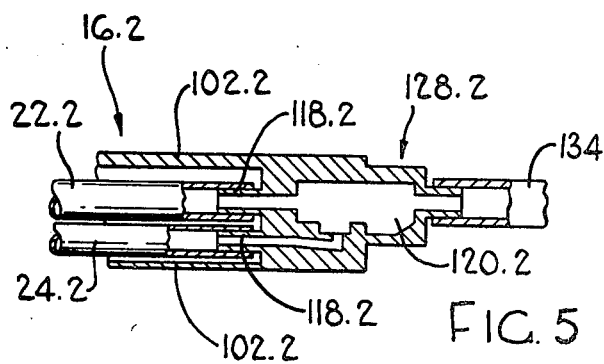
FIG. 5 shows, to an enlarged scale, a fragmentary, partly sectional view along line V—V of FIG. 4, of portion of the fluent material pack of FIG. 4.

With particular reference to FIGS. 4 and 5 of the drawings, reference numeral 14.2 refers generally to an alternative embodiment of a fluent material pack in accordance with this invention, which can be used in place of the fluent material pack 14.1 where an injectable veterinary solution or slurry is to be dispensed.

The fluent material pack 14.2 corresponds substantially with the pack 14.1. Corresponding parts are therefore indicated by corresponding reference numerals, except that the suffix '0.2' has been used in place of the suffix '0.1'.

In place of the dispensing nozzle 116.1, the fluent material pack 14.2 has a single discharge tube 134 leading from the casing 128.2.

The discharge tube 134 has a floating needle 136 sealingly mounted at its free end.

The floating needle 136 is shaped to be conveniently handled by hand, and has a thumb-receiving flange flange 138.

The floating needle 136 has a spring-biassed one-way valve (not shown) located within its bore to combat discharge of fluent material under the action of gravity when the fluent material pack 14.2 is not in use.

The floating needle 136 is shown having a conventional needle 140 mounted thereon by means of a conventional type of threaded cap 142.

The threaded cap 142 may conveniently be such that prior to fitting of the needle 140, the floating needle 136 will be sealed by the threaded cap. Thus, the fluent material pack 14.2 comprising the collapsible container 132.2 the dispensing tubes 22.1 and 24.1, the cartridge 16.2 and the floating needle 136 will be maintained in a sealed hygienic condition for storage and transportation prior to use. It will be appreciated that if the container 130.2 is not fixed to the tube 22.2, the tube 22.2 will also be appropriately sealed prior to use.

The embodiment of the invention as illustrated in FIGS. 4 and 5 of the drawings, can therefore provide the further advantage that once the veterinary remedy contained in the container 132.2 has been used up, the fluent material pack 14.2 can be disposed of entirely. In this way inadvertent use of a contaminated remedy, and re-use of a contaminated fluent material pack or any components thereof, will tend to be avoided.

As can be seen in particular in FIG. 5 of the drawings, the casing 128.2 has the two inlet sleeves 118.2 to which the tubes 22.2 and 24.2 are fixed. The inlet sleeves 118.2 lead to the mixing chamber 120.2.

Figure 10:
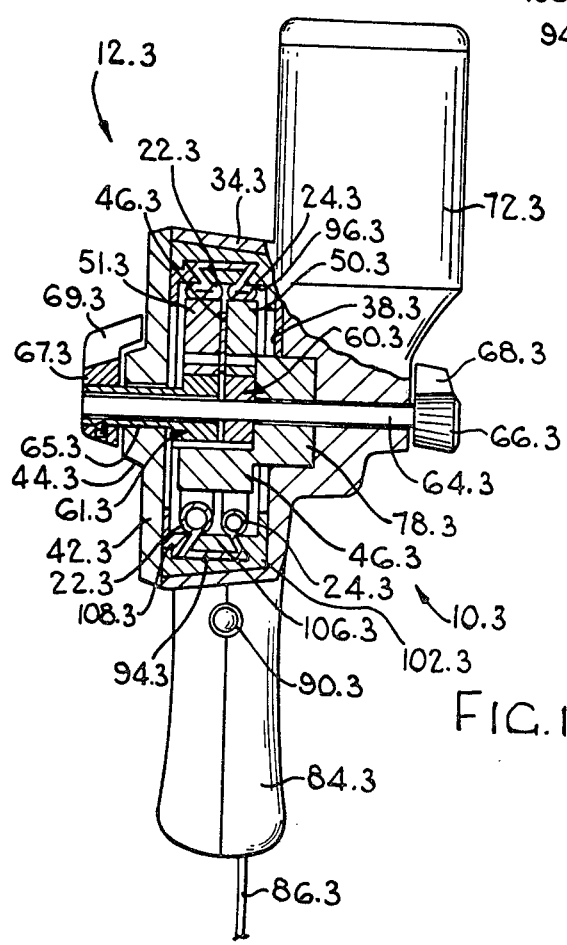
FIG. 10 shows a diagrammatic, partly sectional, front elevation of an alternative embodiment of a dispensing kit in accordance with this invention.

With reference to FIG. 10 of the drawings, reference numeral 12.3 refers generally to an alternative embodiment of a dispensing kit in accordance with this invention. The dispensing kit 12.3 corresponds substantially with the dispensing kit 12.1 and corresponding parts are therefore indicated by corresponding reference numerals, except that the suffix '0.3' has been used in place of the suffix '0.1'.

The dispensing kit 12.3 differs from the dispensing kit 12.1 in that the dispensing device 10.3 has a double adjustment means in place of the single adjustment means of the dispensing device 10.1.

The double adjustment means of the dispensing device 10.3 comprises two independently adjustable cam members 60.3 and 61.3, which are arranged to co-operate separately with two separate radially displaceable compression members 50.3 and 51.3 which are slidably connected to the rotary member 46.3.

The compression members 50.3 and 51.3 are mounted on the rotary member 46.3 in the corresponding manner to that in which the compression member 50.1 is mounted on the rotary member 46.1.

As can be seen in the drawing, the compression member 50.3 is arranged to co-operate with the dispensing tube 24.3, whereas the compression member 51.3 is arranged to co-operate with the dispensing tube 22.3.

The adjustable cam member 60.3 corresponds with the adjustable cam member 60.1, except that it has been shortened so that it will co-operate only with the compression member 50.3.

The cam member 61.3 has a cam surface corresponding to that of the cam surface 62.3 of the cam member 60.3.

The cam member 61.3 is integrally mounted on a hollow adjustment shaft 65.3 which extends slidably through a bore provided in the cover plate 42.3.

An adjustment knob 67.3, having an adjustment pointer 69.3, is mounted on the free end of the hollow adjustment shaft 65.3. Therefore, by adjusting the adjustment knob 67.3 the position of the cam member 61.3 can be adjusted as required to adjust the effective length of the compression path effected by the compression member 51.3 during a revolution of the rotary member 46.3.

The adjustment shaft 64.3 extends slidably through the hollow adjustment shaft 65.3 so that the adjustment shaft 64.3 as well as the hollow adjustment shaft 65.3 are securely supported, and thus the cam members 60.3 and 61.3 are securely supported.

The embodiment of the dispensing kit 12.3 as illustrated in FIG. 10 of the drawings, therefore provides the advantage that the adjustable cam members 60.3 and 61.3 can be adjusted independently to adjust the effective lengths of the compression paths which are effected by the compression members 50.3 and 51.3 during each revolution of the rotary member 46.3.

Thus, in the embodiment illustrated in FIG. 10, the relative proportions between two fluent materials dispensed through the dispensing tubes 22.3 and 24.3, will depend not only on the relative cross-sectional areas of the dispensing tubes, but also on the specific adjustments of the cam members 60.3 and 61.3. Thus, the relative proportions of fluent materials dispensed through the tubes can be adjusted over a wide range, and the specific dosage rates required can be adjusted by adjusting the number of revolutions performed by the rotary member 46.3 for each actuation of the control means by the trigger 90.3.

With reference to FIGS. 11 and 12 of the drawings, reference numeral 12.4 refers to yet a further alternative embodiment of a dispensing kit in accordance with this invention.

The dispensing kit 12.4 corresponds substantially with the dispensing kit 12.1 and corresponding parts are therefore indicated by corresponding reference numerals, except that the suffix '0.4' is used instead of the suffix '0.1'.

In the dispensing kit 12.4, the dispensing device 10.4 has a single cam member 60.4 which corresponds exactly with the cam member 60.1. However, in place of the single compression member 50.1, the rotary member 46.4 has a pair of radially displaceable compression members 50.4 and 51.4 mounted on the rotary member 46.4 in axially spaced positions.

The compression members 50.4 and 51.4 thus both co-operate with the cam member 60.4.

The compression members 50.4 and 51.4 project to differing extents beyond the periphery of the rotary member 46.4 for co-operating with dispensing tubes 22.4 and 24.4 which are located along different radii of curvature in the cartridge zone by the cartridge 16.4.

Since the dispensing tubes 22.4 and 24.4 are located along different radii of curvature, their effective lengths presented for compression by the compression members 51.4 and 50.4 during use, will be different.

Thus, as in the case of the dispensing kit 12.3, the relative proportions of fluent materials dispensed through the dispensing tubes during use will depend not only on the relative proportions of their cross-sectional areas, but also on the relative proportions of their effective lengths presented for compression.

The embodiment of the invention as illustrated in FIG. 11 of the drawings, provides the advantage that by selecting a cartridge having appropriate relative proportions between the effective lengths of the dispensing tubes which are presented for compression during use, the appropriate ratio between the two fluent materials to be dispensed, can be obtained.

The embodiment as illustrated in FIG. 11 of the drawings, provides the further advantage that since the compression members 50.4 and 51.4 are independent, adequate and effective compression of the dispensing tube 22.4 and 24.4 will be obtained even if the wall thicknesses of the one tube are slightly oversize and the wall thicknesses of the other tube are slightly undersize.

With reference to FIG. 13 of the drawings, reference numeral 16.5 refers to an alternative embodiment of a cartridge for use with the dispensing device 10.1.

The cartridge 16.5 is shown having two dispensing tubes 22.5 and 24.5 mounted thereon.

The cartridge 16.5 has two separate compression surfaces against which the tubes can be compressed during use.

The one compression surface against which the dispensing tube 24.5 is compressed during use, is in the form of an arc through 180° which has a constant radius, thereby permitting compression of the tube 24.5 throughout the entire arc of 180° during use.

However, insofar as the dispensing tube 22.5 is concerned, the compression surface 96.5 of the cartridge 16.5 extends only through an arc of 45° at a constant radius. Thus, the compression tube 22.5 will be compressed during use only through the arc of 90°.

The remainder of the compression surface 96.5 is recessed so that the surface 97 is at a radius greater than the radius of the surface 96.5.

It follows therefore that during use of the cartridge 16.5, the dispensing tube 22.5 will not be compressed in the zone where it is in contact with the surface 97.

It follows therefore that if the tubes 22.5 and 24.5 have exactly the same cross-sectional bore area, the quantity of fluent material dispensed through the dispensing tube 24.5 will be double the quantity dispensed through the dispensing tube 22.5 during each revolution of a rotary member of the dispensing device.

The embodiment as illustrated in FIG. 13 of the drawing, provides the advantage that cartridges 16.5 can be designed which have required relationships between the effective lengths of their compression surfaces and which therefore provide the required relationships between the effective lengths of the dispensing tubes presented for compression during use, and thus for the relative proportions of fluent materials dispensed during use.

Figure 14:
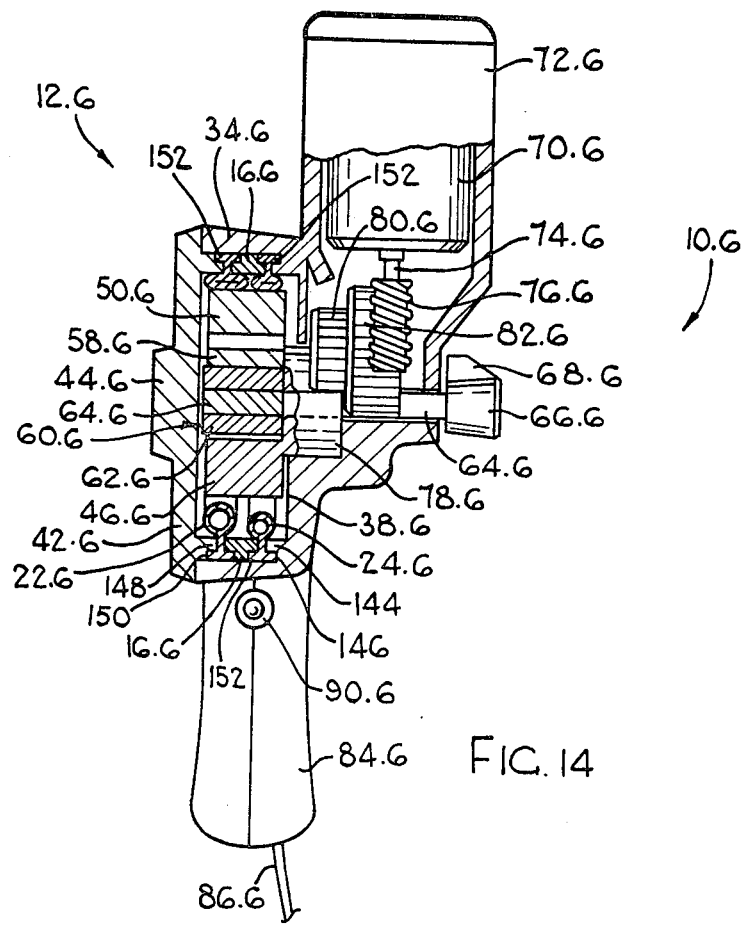
FIG. 14 shows a diagrammatic, fragmentary, partly sectional front elevation of yet a further alternative embodiment of a dispensing kit in accordance with this invention.

With reference to FIG. 14 of the drawings, reference numeral 12.6 refers to yet a further alternative embodiment of a dispensing kit in accordance with this invention.

The dispensing kit 12.6 corresponds generally with the dispensing kit 12.1 and corresponding parts are therefore indicated by corresponding reference numerals, except that the suffix '0.6' has been used in place of the suffix '0.1'.

In the embodiment illustrated in FIG. 14, the dispensing device 10.6 has a locating shoulder 144 provided between the peripheral wall 34.6 and the base wall 38.6.

The locating shoulder 144 has a locating formation in the form of a locating groove 146 provided therein.

The cover plate 42.6 has a locating flange 148, depending therefrom. The locating flange has a locating groove 150 provided therein. The locating groove 150 has a cross section corresponding to that of the locating groove 146.

The cartridge 16.6 is in the form of an annular ring which has locating groove formations along its opposed ends which are complementary to the locating grooves 146 and 150.

The dispensing tubes 22.6 and 24.6 are separate, and each dispensing tube has an engagement flange 152 of T-section integrally formed therewith.

In use, for locating the dispensing tubes 22.6 and 24.6 in the cartridge zone of the housing of the dispensing device 10.6, the engagement flange 152 of the dispensing tube 22.6 can be located in the locating groove 146, thereafter the cartridge 16.6 can be located in position to trap the engagement flange between it and the locating shoulder 144.

Thereafter, the engagement flange 152 of the dispensing tube 24.6 can be located in the locating formation of the cartridge 16.6, and the cover plate 42.6 can be mounted in position so that the engagement flange 152 of the dispensing tube 24.6 is trapped in position between the cartridge 16.6 and the locating flange 148.

It will be appreciated that, if desired, the engagement flanges 152 of the dispensing tubes may be secured to the cartridge 16.6 by means of an adhesive or the like to facilitate loading.

It will further be appreciated that, if desired, the engagement flanges 152 of the two dispensing tubes 24.6 and 22.6 may be integrally connected. In this embodiment, the cartridge 16.6 will be shaped to accommodate the integrally connected portions of the engagement flanges 152.

The embodiment of the invention as illustrated in FIG. 14 of the drawings, provides the advantage that the cartridge 16.6 can be manufactured more cheaply than the cartridges of the remaining embodiments, and yet the cartridge 16.6 will be effective in firmly locating the dispensing tubes in position in the dispensing device, for use.

Figure 15:
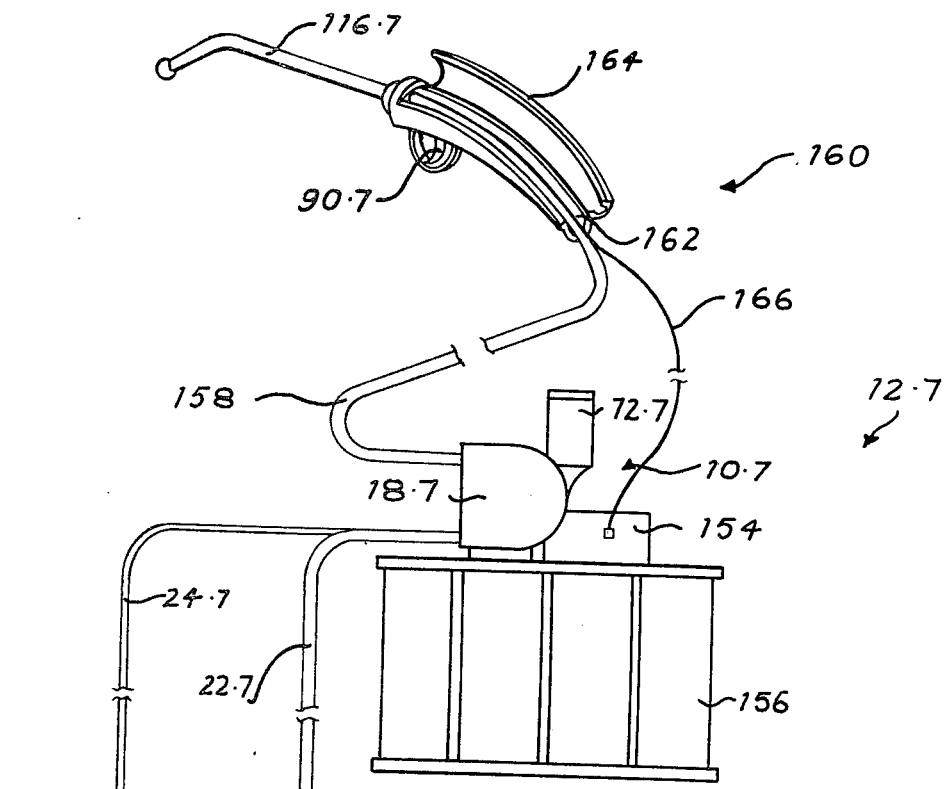
FIG. 15 shows a diagrammatic, fragmentary view of yet a further alternative embodiment of a dispensing kit in accordance with this invention.

With reference to FIG. 15 of the drawings, reference numeral 12.7 refers to yet a further alternative embodiment of a dispensing kit in accordance with this invention.

The dispensing kit 12.7 corresponds generally with the dispensing kit 12.1, and corresponding parts are therefore indicated by corresponding reference numerals, except that the suffix '0.7' is used in place of the suffix '0.1'.

The dispensing kit 12.7 includes a dispensing device 10.7 which differs from the dispensing device 10.1 in that in place of the handle 84.1, it has a housing box 154 wherein the control means is housed.

The dispensing device 10.7 is removably mounted on a battery 156 via the housing box 154.

The dispensing tubes 22.7 and 24.7 are located in the dispensing device 10.7 by means of a suitable cartridge, and a single discharge 158 leads out of the dispensing device 10.7.

The dispensing kit 12.7 includes an actuating member 160.

The actuating member 160 has a dispensing nozzle 116.7 integrally formed therewith, and has the free end of the discharge tube 158 sealingly connected to the dispensing nozzle 116.7.

The actuating member includes an elongated groove 162 wherein the discharge tube is supported.

The actuating member 160 further has a displaceable lid 164 (shown in its open position) which can be closed for firmly locating the discharge tube 158 in position in the groove 162.

The actuating member 160 further has a trigger 90.7 which is connected by means of a lead 166 to the control means in the housing box 154.

The actuating member 160 is shaped to be suitable to be held by hand.

The length of the discharge tube 158 and the lead 166 may therefore be such that the actuating member 160 can be handled at a point remote from the remainder of the dispensing kit 12.7.

The embodiment of the invention as illustrated in FIG. 15 of the drawings, provides the advantage that the dispensing kit 12.7 can be placed in a suitable location, and the actuating member 160 can then be used at a point remote therefrom to actuate the dispensing device 10.7, and to apply fluent materials to be dispensed, through the dispensing nozzle 116.7.

Figure 16:
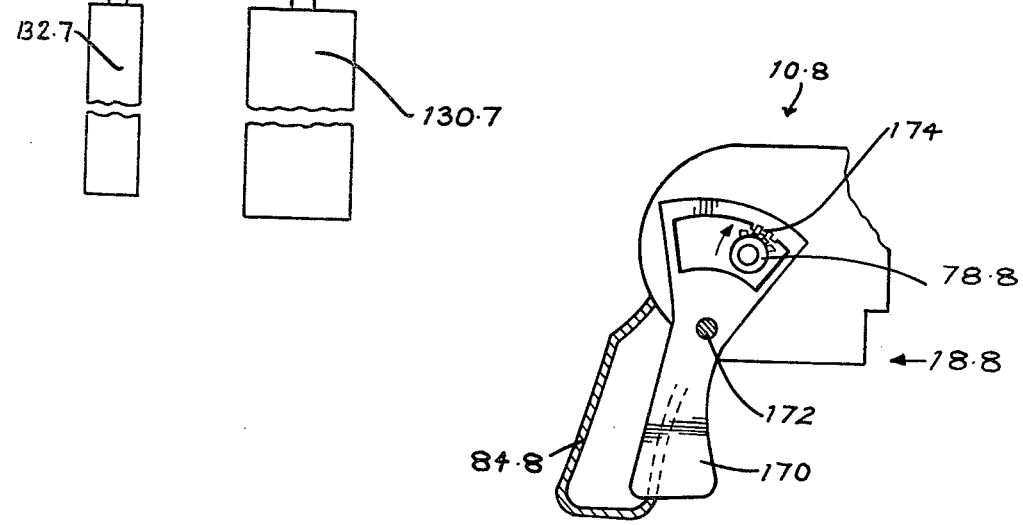
FIG. 16 shows a fragmentary, diagrammatic view of yet a further alternative embodiment of a dispensing device in accordance with this invention.

With reference to FIG. 16 of the drawings, reference numeral 10.8 refers generally to an alternative embodiment of a dispensing device in accordance with this invention.

The dispensing device 10.8 corresponds generally with the dispensing device 10.1 except that in place of the drive means 32.1, the dispensing device 10.8 includes a manually operable lever for displacing the collapsing means during use.

The lever 170 is pivotally mounted in the handle 84.8 about a pivot pin 172.

The lever 170 is provided with a linear gear 174 to co-operate with the annular gear 78.8 of the rotary member of the dispensing device 10.8.

The lever 170 includes a return spring (not shown) to return the lever to its starting position. It further includes a suitable directional clutch or the like (not shown), to release the annular gear 78.8 from the rotary member during return of the lever 170 to its starting position.

In use, when the handle 84.8 is held in the hand of an operator, finger pressure can be applied to the lever 170 to displace it about the pivot pin 172. During such displacement the linear gear 174 co-operates with the annular gear 78.8 to rotatably drive the annular gear 78.8 and thus the rotary member of the dispensing device 10.8.

It will be appreciated that there are practical limitations on the extent to which displacement of the lever 170 can rotate the rotary member of the dispensing device 10.8. In practice therefore, unless a complex gear train system is employed, it may be found that for each displacement of the lever 170, it is only practical to have the rotary member rotatably driven through one revolution or possibly two revolutions.

The embodiments of the invention as illustrated in the drawings, can provide the further advantage that where only portion of the concentrated veterinary remedy has been used, the fluent material pack can be resealed for later use without the remaining portion having become contaminated or diluted with water. Thus, the preservatives remaining in that remaining portion of the concentrated veterinary remedy should therefore be sufficient to preserve it for future use.

While the embodiments of the invention as illustrated in the drawings, have been described with reference to the dilution of a veterinary remedy which is applied as an injectable solution, as an oral dosing solution or as a spot-on solution, it will be appreciated that the dispensing kit of this invention may be applied equally to the dispensing of various other types of fluent materials. In addition, it may be used not merely for dilution but also for the mixing of different fluent materials in appropriate proportions.

It follows from the embodiments of the invention as illustrated in the drawings, that the relative proportions of fluent materials dispensed through the dispensing tube by means of the dispensing kit of this invention, may be varied by using dispensing tubes of differing cross-sectional areas, by using tubes having differing effective compression lengths, and by using a plurality of adjustable cams which are independently adjustable.

In practice, particularly for veterinary remedies, the simplest procedure would probably tend to be to provide each active ingredient which is to be dispensed, in a desired concentration form for dilution when it is dispensed, and then selecting tube cross-sectional bore areas which will provide for the proportion of active ingredient to water dispensed during use to be in the correct relationship.

The embodiments of the invention as illustrated in the drawings, provide the essential advantage that by having the dispensing tubes associated with a cartridge, loading and unloading is greatly facilitated, and incorrect loading is prevented. In addition, the cartridge serves to locate the dispensing tubes securely within the dispensing device so that they are always in the appropriate position for compression by means of the compression member or members, and so that they will be held securely against any tendency to creep in the downstream direction of the tubes during use.

I claim:

1. A dispensing device for use in dispensing measured quantities of fluent materials through a plurality of resiliently compressible dispensing tubes, the device comprising a housing having a cartridge zone for receiving a cartridge having a plurality of dispensing tubes associated therewith;
    a rotatably displaceable collapsing means for collapsing, in compression zones, dispensing tubes when located in the cartridge zone by means of a cartridge, said collapsing means including a plurality of radially displaceable compression members which are slidably connected to the collapsing means;
    drive means for rotatably driving the collapsing means to advance the compression zone along compression paths to dispense fluent material through such dispensing tubes;
    adjustment means including a plurality of independently adjustable cam members to cooperate with the respective compression members and control the effective length of the compression paths during a revolution of the collapsing means.

2. A device according to claim 1, including control means for controlling operation of the drive means, the control means being adjustable to allow the collapsing means to be rotatably driven through a selected angle upon each actuation of the drive means.

3. A device according to claim 1, in which the drive means comprises a displaceable lever member.

4. A device according to claim 1, in which the drive means comprises an electric motor.

5. A device according to claim 1, in which the collapsing means includes a plurality of radially displaceable compression members which are slidably connected to the collapsing means to project to differing extents beyond the periphery of the collapsing means for co-operating with dispensing tubes when located along different radii of curvature in the cartridge zone by a cartridge.

6. A device according to any one of claim 1, in which the housing has a supporting formation for supporting a dispensing nozzle on the housing.

7. A dispensing kit including a dispensing device for use in dispensing quantities of fluent material through a plurality of resiliently compressible dispensing tubes, the device comprising a housing having a cartridge zone for receiving a cartridge having a plurality of dispensing tubes associated therewith;
    collapsing means for collapsing, in compression zones, dispensing tubes when located in the cartridge zone by means of a cartridge;
    and, displacement means for displacing the collapsing means to advance the compression zones along compression paths to dispense fluent materials through such dispensing tubes;
    including a cartridge removably located in the cartridge zone;
    and including a plurality of resiliently compressible dispensing tubes located in the cartridge zone by means of the cartridge;
    said cartridge comprising an annular ring member, said cartridge zone having an annular recess defined in part by a cover plate for the cartridge zone, each dispensing tube having an engagement flange, each dispensing tube being located in the cartridge zone by having its engagement flange trapped in the annular recess by the ring member located in the annular recess.

8. A dispensing kit including a dispensing device for use in dispensing measured quantities of fluent materials through a plurality of resiliently compressible dispensing tubes, the device comprising a housing having a cartridge zone for receiving a cartridge having a plurality of dispensing tubes associated therewith; collapsing means for collapsing, in compression zones, dispensing tubes when located in the cartridge zone by means of a cartridge; and displacement means for displacing the collapsing means to advance the compression zones along compression paths to dispense fluent materials through such dispensing tubes; including a cartridge removably receivable in the cartridge zone; and including a plurality of resilienty compressible dispensing tubes associated with the cartridge for positive location in the cartridge zone.

9. A dispensing kit according to claim 7, in which the cartridge comprises a body portion having a bore defined by a curved compression wall, and in which the dispensing tubes are associated with the compression wall for compression against it by the collapsing means during use.

10. A dispensing kit according to claim 7, in which at least one dispensing tube is integrally connected to a collapsible fluent material container.

11. A dispensing kit according to claim 7, in which the cartridge has a dispensing nozzle integrally mounted thereon, and in which the dispensing tubes lead to the nozzle.

12. A dispensing kit according to claim 7, in which the dispensing tubes form a common discharge tube beyond the cartridge, and in which the discharge tube has a needle mounted at its free end.

13. A dispensing kit according to claim 7, in which the cartridge includes a one-way valve having a valve closure member which is biassed to combat discharge of fluent materials through the dispensing tubes under gravity.

14. A dispensing kit according to claim 7, in which the dispensing tubes are associated with the cartridge such that their effective lengths presented for compression during use, will differ.

15. A dispensing device for use in dispensing measured quantities of fluent materials through a plurality of resiliently compressible dispensing tubes, the device comprising a housing having a cartridge zone for receiving a cartridge having a plurality of dispensing tubes associated therewith;

collapsing means including a plurality of displaceable compression members which are slidably connected to the collapsing means for collapsing, in compression zones, dispensing tubes when located in the cartridge zone by means of a cartridge;

a displacement means for displacing the collapsing means to advance the compression zone along compression paths to dispense fluent material through such dispensing tubes; and, adjustment means including adjustable cam means to cooperate with at least one compression member and control the effective length of at least one of the compression paths during the operation of the collapsing means.

16. The device according to claim 15 wherein said cam means cooperates with both compression members and controls the effective length of both compression paths during the operation of the collapsing means.

17. The device according to claim 15 in which the adjustment means includes a plurality of independently adjustable cam members to cooperate with the respective compression members and wherein the cam members are adjustable to provide the control of the effective length of the compression path during operation of the collapsing means.

* * * * *